(12) United States Patent
Chimote et al.

(10) Patent No.: US 8,697,653 B2
(45) Date of Patent: Apr. 15, 2014

(54) MICROPARTICLE FORMULATION FOR PULMONARY DRUG DELIVERY OF ANTI INFECTIVE MOLECULE FOR TREATMENT OF INFECTIOUS DISEASES

(75) Inventors: Geetanjali Chandrashekhar Chimote, Mumbai (IN); Girish Badrinath Mahajan, Mumbai (IN); Aravindan Vasudevan, Mumbai (IN); Sivaramakrishnan Hariharan, Mumbai (IN)

(73) Assignee: Priamal Enterprises Limited, Mumbai (IN)

( * ) Notice: Subject to any disclaimer, the term of this patent is extended or adjusted under 35 U.S.C. 154(b) by 0 days.

(21) Appl. No.: 13/813,470

(22) PCT Filed: Aug. 4, 2011

(86) PCT No.: PCT/IB2011/053470
§ 371 (c)(1),
(2), (4) Date: Jan. 31, 2013

(87) PCT Pub. No.: WO2012/017405
PCT Pub. Date: Feb. 9, 2012

(65) Prior Publication Data
US 2013/0125879 A1  May 23, 2013

Related U.S. Application Data

(60) Provisional application No. 61/370,916, filed on Aug. 5, 2010.

(51) Int. Cl.
*A61K 38/12* (2006.01)

(52) U.S. Cl.
USPC ...... 514/21.1; 424/400; 424/450; 128/200.14; 264/6

(58) Field of Classification Search
USPC ............. 514/21.1; 424/400, 450; 128/200.14; 264/6
See application file for complete search history.

(56) References Cited

U.S. PATENT DOCUMENTS 4,877,561 A   10/1989   Iga et al.

FOREIGN PATENT DOCUMENTS

| WO | 2001/054693 A1 | 8/2001 |
| WO | 2011/027290 A1 | 3/2011 |

OTHER PUBLICATIONS

K. C. Nicolaou et al.; "Discovery of a Biologically Active Thiostrepton Fragment."; Journal of the American Chemical Society; Nov. 2, 2005; LNKD-PUBMED:16248640; vol. 127; No. 3; pp. 15042-15044; XP002660803; ISSN: 0002-7863; the whole document.

*Primary Examiner* — Raymond Henley, III
(74) *Attorney, Agent, or Firm* — Ladas & Parry LLP

(57) ABSTRACT

The present invention relates to a biodegradable, inhalable microparticle formulation comprising a compound of formula I obtained by fermentation of a microorganism of the *Streptomyces* species (PM0626271/MTCC5447), as described in PCT application publication WO2011027290, and a biodegradable lipid for drug delivery wherein the ratio of drug (compound of formula I) to lipid is 1:15 to 1:25. The present invention also relates to the process for preparation of the formulation and to the method of treatment of pulmonary tuberculosis, multi drug resistant tuberculosis (MDRTB), methicillin resistant *Staphylococcus aureus* (MRSA) pneumonias and methicillin sensitive *Staphylococcus aureus* (MSSA) pneumonias by administering therapeutically effective amount of the formulation to a mammal in need thereof. The present invention further relates to a method of delivering the microparticle formulation to a mammal in need thereof, wherein the formulation is administered by inhalation or intratracheal instillation for pulmonary delivery.

20 Claims, No Drawings

MICROPARTICLE FORMULATION FOR PULMONARY DRUG DELIVERY OF ANTI INFECTIVE MOLECULE FOR TREATMENT OF INFECTIOUS DISEASES

RELATED APPLICATION INFORMATION

This application is a 371 of International Application PCT/IB2011/053470 filed 4 Aug. 2011 entitled "Microparticle Formulation For Pulmonary Drug Delivery Of Anti Infective Molecule For Treatment Of Infectious Diseases", which was published in the English language on 9 Feb. 2012, with International Publication Number WO 2012/017405 A1, and which claims priority from U.S. Patent Application 61/370,916 filed 5 Aug. 2010, the content of which is incorporated herein by reference.

FIELD OF THE INVENTION

The present invention relates to a biodegradable, inhalable microparticle formulation comprising a compound obtained by fermentation of a microorganism of the *Streptomyces* species (PM0626271/MTCC5447), as described in PCT application publication WO 2011027290, hereinafter referred to as compound of formula I, and a biodegradable lipid for drug delivery wherein the ratio of drug (compound of formula I) to lipid is 1:15 to 1:25. The present invention also relates to a method of treatment of pulmonary tuberculosis, multi drug resistant tuberculosis (MDRTB), methicillin resistant *Staphylococcus aureus* (MRSA) pneumonias and methicillin sensitive *Staphylococcus aureus* (MSSA) pneumonias by administering therapeutically effective amount of the formulation to a mammal in need thereof. The present invention also relates to the use of the microparticle formulation for the treatment of pulmonary tuberculosis, MDRTB, MRSA pneumonias and MSSA pneumonias.

BACKGROUND OF THE INVENTION

Tuberculosis can affect any organ of the body and is manifested in several different forms, but the primary site of infection is the lung. Tuberculosis affecting the lungs is known as pulmonary tuberculosis. Pulmonary tuberculosis is the most predominantly occurring form of tuberculosis (Tuberculosis, 2005, 85, 227-234). The current chemotherapeutic regimen for treating pulmonary tuberculosis consists of co-administration of front-line antitubercular drugs (isoniazid, rifampicin, ethambutol, and/or pyrizinamide) for a period of four months followed by two months of treatment with isoniazid, rifampicin, and/or ethambutol, but depending upon the type of tuberculosis, the treatment can be further extended upto a period ranging from 9 months to 2 years. This current chemotherapeutic regimen is given in the form of once a day oral dosing, which is associated with poor plasma half-life (International Journal of Pharmaceutics, 2004, 276, 41-49) and a plethora of dose related adverse effects (Journal of Antimicrobial Chemotherapy, 2004 54, 761-766). These adverse effects are attributed to an undesirable biodistribution profile. Moreover, in respect of the orally administered drugs it has been observed that only a small fraction of the drug reaches the site of action i.e. the lungs and is cleared within hours (Tuberculosis, 2005, 85, 227-234). The above problems are associated with poor patient compliance and result in the development of multidrug resistant tuberculosis (MDRTB).

MDRTB is a form of tuberculosis that is resistant to at least two of the best antitubercular drugs, isoniazid and rifampicin (Multidrug resistant tuberculosis fact sheet, Center for Disease Control, 2008). MDRTB is treated with second line antitubercular drugs like fluoroquinolones, aminoglycosides like amikacin, kanamycin, capreomycin, para-aminosalicyclic acid and thioacetazone (Treatment of drug resistant tuberculosis, fact sheet, Center for Disease Control, 2007). The second line tuberculosis drugs are associated with dose related side effects, poor bioavailability in the lungs, which is detrimental for disease eradication.

Analogous to the problem of pulmonary tuberculosis, the problems of poor bioavailability of drugs and higher dose induced adverse effects are also encountered in the treatment of MRSA and MSSA pneumonias. Nosocomial pneumonias and ventilator-associated pneumonias resulting from MRSA are associated with high mortality rates (International Journal of Antimicrobial Agents, 2007, 30, 19-24), the reason for the aforesaid being inadequate treatment.

First line drugs that are used to treat MRSA pneumonia include vancomycin and linezolid. Vancomycin, the drug of choice for treating MRSA pneumonia, is associated with unsatisfactory pharmacokinetic profile in the lung tissue and has lung concentrations, which are just 20% of the plasma concentrations (Antimicrob. Agents Chemother., 1999, 37, 281-286). Moreover, long-term administration of vancomycin is associated with nephrotoxicity, which is a dose-limiting factor (Clin. Microbiol. Infect., 2006, 12, 92-95). Linezolid, which is accepted for therapy in MRSA pneumonia, exhibits good oral bioavailability (administered as 600 mg oral twice daily) but is associated with gastrointestinal adverse effects, thrombocytopenia, and reversible anemia (Clinical Infect. Dis., 2003, 37, 1609-1616). On rare occasions, administration of linezolid is also associated with optic and peripheral neuropathy (J. Antimivrob. Chemother., 2004, 53, 1114-1115).

Beta lactam agents (such as ampicillin and cepholosporins) are very effective against MSSA pneumonia as first line of therapy. Though vancomycin is considered as next line of therapy, it is not as effective as the beta lactam agents in infections caused by MSSA. Also vancomycin is excreted in the urine by glomerular filtration and is not metabolized. Lung tissue penetration of vancomycin is also relatively poor (US Respiratory Disease, 2006, 62-64). In summary, the therapy for MRSA/MSSA pneumonia has several drawbacks such as poor pulmonary bioavailability of drugs, drug dosage induced toxicity, etc.

To overcome the problems associated with the current standard treatment regimen and patient non-compliance, it is essential to develop a drug delivery system that directly reaches the site of action, has the potential to target the lung macrophages where mycobacteria reside and reduce drug associated systemic toxicity.

SUMMARY OF THE INVENTION

The present invention relates to a biodegradable, inhalable microparticle formulation comprising compound of formula I (as described herein) obtained by fermentation of a microorganism of the *Streptomyces* species (PM0626271/MTCC5447), and a biodegradable lipid for drug delivery wherein the ratio of drug (compound of formula I) to lipid is from 1:15 to 1:25.

The present invention also relates to the process for preparation of the microparticle formulation.

The present invention further relates to the method of treatment of pulmonary tuberculosis, MDRTB, MRSA pneumonias and MSSA pneumonias by administering a therapeutically effective amount of the microparticle formulation to a mammal in need thereof.

The present invention also relates to a method of delivering the microparticle formulation to a mammal in need thereof, wherein the formulation is administered by inhalation or intratracheal instillation for pulmonary delivery.

The present invention further relates to the use of the microparticle formulation comprising compound of formula I and a biodegradable lipid for drug delivery wherein the ratio of drug (compound of formula I) to lipid is 1:15 to 1:25 for the treatment of pulmonary tuberculosis, MDRTB, MRSA pneumonias and MSSA pneumonias.

The present invention further relates to the use of the microparticle formulation comprising compound of formula I and a biodegradable lipid for drug delivery wherein the ratio of drug (compound of formula I) to lipid is 1:15 to 1:25 for the manufacture of a medicament for the treatment of pulmonary tuberculosis, MDRTB, MRSA pneumonias and MSSA pneumonias.

DETAILED DESCRIPTION OF THE INVENTION

Before describing the present invention in detail, it has to be understood that this invention is not limited to particular embodiments. It is also to be understood that the terminology used herein is for the purpose of describing particular embodiments only, and is not intended to be limiting.

As used in the specification and claims, the singular forms "a", "an" and "the" include plural references unless the context clearly indicates otherwise.

Unless defined otherwise, all technical and scientific terms used herein have the same meaning as commonly understood by one of the ordinary skill in the art to which the invention belongs.

DEFINITIONS

Entrapment efficiency: Entrapment efficiency is the fraction of drug associated and physically entrapped in the microparticle formulation relative to the initial total amount of drug in the solution.

Drug: A drug is defined as any substance intended for use in the diagnosis, cure, relief, treatment or prevention of disease or intended to affect the structure or function of the body. As used herein compound of formula I is a drug.

Mass balance: A mass balance (also called a material balance) is an application of conservation of mass to the analysis of physical systems. By accounting for material entering and leaving a system, mass flows can be identified which might have been unknown, or difficult to measure without this technique.

Osmolality: Osmolality is a measure of solute concentration, defined as the number of osmoles (mOsm) of solute per kilogram of solvent (mosmol/kg or mOsm/kg).

Phase Transition: A phase transition is the transformation of a thermodynamic system from one phase or state of matter to another. A phase of a thermodynamic system and the states of matter have essentially uniform physical properties. During a phase transition of a given medium certain properties of the medium change, often discontinuously, as a result of some external condition, such as temperature, pressure, and others. The measurement of the external conditions at which the transformation occurs, is termed as the phase transition point.

Aerosolization: Aerosolization is the production of an aerosol—a fine mist or spray containing minute particles.

Nebulization: Nebulization involves the process of transforming liquid medications into faster-acting inhaled mists. Nebulization is used to treat respiratory conditions, such as asthma or cystic fibrosis. Nebulizers effectively deliver medicine directly into an individual's respiratory tract so that it can reach the lungs quickly. A non-limiting example of nebulizer is a machine equipped with a compressor and a mouthpiece or face mask.

Particle Size Particle size is a notion introduced for comparing dimensions of solid particles, liquid particles (droplets). For droplets and aerosols, terms such as "aerodynamic diameter" and "mass median aerodynamic diameter (MMAD) are used. The definitions are given below.

Aerodynamic diameter: The diameter of a unit-density sphere having the same terminal settling velocity as the particle in question. It is used to predict where in the respiratory tract such particles will deposit.

Mass Median Aerodynamic Diameter: The geometric mean aerodynamic diameter. Fifty percent of the particles by weight will be smaller than the MMAD, 50% will be larger.

During particle sizing experiment, the suspensions contain innumerable number of particles of varying sizes in motion. When the particle-sizing machine analyzes these particles, it forms a particle distribution curve, which covers the entire particle size range starting from the smallest particle, which could be 1 nm to the largest, which could be 100 microns. In the particle size distribution curve, a cumulative frequency is calculated for the particles. $D_{10}$ refers to that particular particle diameter where 10% of the particles in the suspension have a smaller diameter or equal diameter as that of the particular particle diameter.

$D_{50}$: Similar to the $D_{10}$, $D_{50}$ is the cut off diameter for 50% of the particle population in the formulation and refers to that particular particle diameter where 50% of the particles in the suspension have a smaller diameter or equal diameter as that of the particular particle diameter.

$D_{90}$: $D_{90}$ is the cut off diameter for 90% of the particle population in the formulation and refers to that particular particle diameter where 90% of the particles in the suspension have a smaller diameter or equal diameter as that of the particular particle diameter.

Entrapped drug retention on nebulization: During nebulization process, due to the force induced by the nebulizer some liposomes rupture and the drug leeches out of the formulation and gets retained in the nebulization cup itself. The drug which does not leech out of the formulation during the nebulization process is the actual amount of drug retained in the formulation during nebulization and is designated as "entrapped drug retention". The drug which is lost to/leeched out during the nebulization process is recovered from the nebulization cup. The nebulization cup is washed with a suitable solvent (in this case methanol) and drug retained in the cup is quantified by HPLC or LC-MS.

Liquid Crystalline Phase: It is a distinct phase of matter observed between the crystalline (solid) and isotropic (liquid) states.

Rippled Gel Phase: It is a metastable state between liquid crystalline phase and gel phase.

Intratracheal Instillation It is a method of drug administration wherein the drug is administered through an endotracheal tube or by percutaneous injection into the trachea for the delivery of drugs into the lungs.

Ventilatory support: In medicine, mechanical ventilation is a method to mechanically assist or replace spontaneous breathing. This is achieved by attaching an endotracheal tube of the disease afflicted patient to the ventilator which is designed for the aforesaid purpose. Ventilators work by altering the patient's airway pressure through an endotracheal or tracheostomy tube. Patients with fulminant pneumonia including MRSA pneumonia are subjected to tracheostomy so that their tissue oxygenation is maintained.

Biodegradable lipid: Biodegradable lipid refers to a lipid which is amenable to chemical degradation in vivo (in the human body) either by enzymatic action or by innate occurring biological processes in which the lipid molecule is broken down to its basic constitutive components.

Therapeutically effective amount: Therapeutically effective amount refers to the amount of drug enough to treat and eliminate the infectious organism of interest in the in vivo conditions. The therapeutic amount of compound of formula I present in the microparticle formulation is in the range of 1% to 5% (w/w).

Non-invasive method of treatment: Non-invasive method of treatment refers to methods like nebulization or intratracheal instillation in pre-tracheotomy individuals. The procedure is painless and doesn't require additional medical interventions which include administration of anesthetic agents to relive pain or its associated components.

The present invention relates to a microparticle formulation comprising compound of formula I, and a biodegradable lipid for drug delivery wherein the ratio of drug (compound of formula I) to lipid is from 1:15 to 1:25 and the microparticle formulation is a biodegradable and inhalable formulation.

According to one aspect of the invention, compound of formula I constitutes 1% to 5% (w/w) of the formulation.

The compound of formula I is structurally represented by the following formula:

The compound can be produced from culture no. PM0626271, its mutants and variants, comprising the steps of: growing the culture no. PM0626271 under submerged aerobic conditions in a nutrient medium containing one or more sources of carbon and one or more sources of nitrogen and optionally nutrient inorganic salts and/or trace elements; isolating the compound of formula I, from the culture broth; and purifying the compound of formula I, using purification procedures generally used in the art.

In addition to the specific microorganism described herein, it should be understood that mutants of the microoganism, such as those produced by the use of chemical or physical mutagens including X-rays, U.V. rays etc. and organisms whose genetic makeup has been modified by molecular biology techniques, may also be cultivated to produce the compound.

The medium and/or nutrient medium used for isolation and cultivation of culture no. PM0626271, which produces the compound of formula I, preferably contains sources of carbon, nitrogen and nutrient inorganic salts. The carbon sources are, for example, one or more of starch, glucose, sucrose, dextrin, fructose, molasses, glycerol, lactose, or galactose. Preferred carbon sources are soluble starch and glucose. The sources of nitrogen are, for example, one or more of soybean meal, peanut meal, yeast extract, beef extract, peptone, malt extract, corn steep liquor, gelatin, or casamino acids. Pre- Formula I 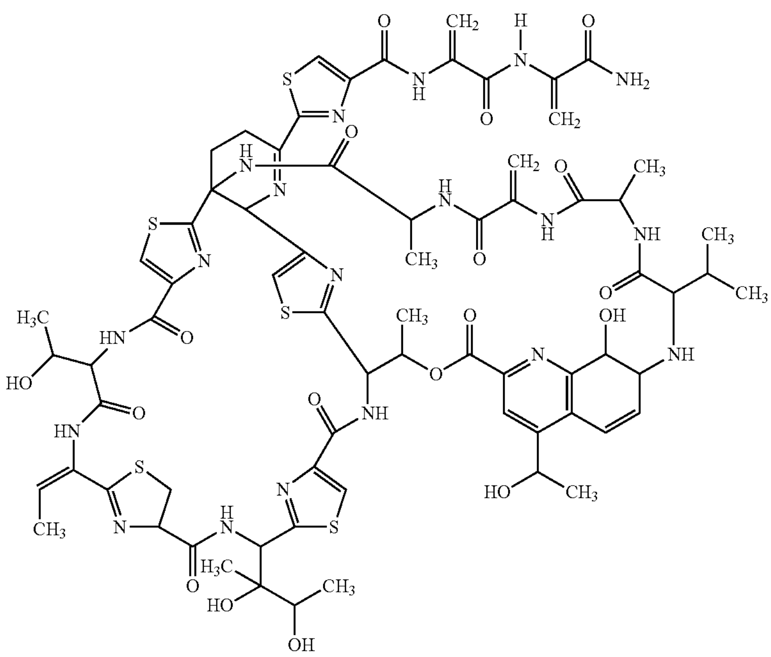 The microorganism, which may be used for the production of the compound of formula I is a strain of *Streptomyces* species (PM0626271/MTCC 5447), herein after referred to as culture no. PM0626271, isolated from a soil sample collected from Schirmacher Oasis in Antarctic region. Culture no. PM0626271 has been deposited with Microbial Type Culture Collection (MTCC), Institute of Microbial Technology, Sector 39-A, Chandigarh-160 036, India, a World Intellectual Property Organization (WIPO) recognized International Depository Authority (IDA) and has accession number MTCC 5447.

ferred nitrogen sources are peptone and yeast extract. The nutrient inorganic salts are, for example, one or more of sodium chloride, potassium chloride, calcium chloride, magnesium chloride, ferric chloride, strontium chloride, cobalt chloride, potassium bromide, sodium fluoride, sodium hydrogen phosphate, potassium hydrogen phosphate, dipotassium hydrogen phosphate, magnesium phosphate, calcium carbonate, sodium bicarbonate, sodium silicate, ammonium nitrate, potassium nitrate, ferrous sulphate, sodium sulphate, ammonium sulphate, magnesium sulphate, ferric citrate, boric acid or trace salt solution such as copper sulphate, manganese chloride or zinc sulphate. Calcium carbonate, sodium chloride, and magnesium chloride are the preferred nutrient inorganic salts.

The maintenance of culture no. PM0626271 may be carried out at a temperature ranging from 22° C. to 36° C. and a pH of about 7.5 to 8.0. Typically, culture no. PM0626271 is maintained at 25° C. to 27° C. and a pH of about 7.4 to 7.8. The well-grown cultures may be preserved in the refrigerator at 4° C. to 8° C.

Seed culture cultivation of culture no. PM0626271 may be carried out at a temperature ranging from 25° C. to 36° C. and a pH of about 7.5 to 8.0 for 66 hours to 75 hours at 200 rpm (revolutions per minute) to 280 rpm. Typically, culture no. PM0626271 seed is cultivated at 29° C. to 31° C. and a pH of about 7.4 to 7.8, for 72 hours at 230 rpm to 250 rpm.

The production of the compound of formula I may be carried out by cultivating culture no PM0626271 by fermentation at a temperature ranging from 26° C. to 36° C. and a pH of about 6.5 to 8.5, for 24 hours to 96 hours at 60 rpm to 140 rpm and 100 lpm (liter per minute) to 200 lpm aeration. Typically, culture no. PM0626271 is cultivated at 30° C. to 32° C. and pH 7.4 to 7.8 for 40 hours to 96 hours at 90 rpm and 110 lpm aeration.

The progress of fermentation and production of the compound can be detected by high performance liquid chromatography (HPLC) and by measuring the bioactivity of the culture broth against Staphylococci and/or Enterococci species by the known microbial agar plate diffusion assay method. The preferred culture is *Staphylococcus aureus* E710, which is a strain resistant to methicillin, a β-lactam antibiotic reported in the literature, and *Enterococcus faecium* R2 (VRE) which is resistant to vancomycin. In the resulting culture broth, the compound may be present in the culture filtrate as well as in cell mass and can be isolated using known separation techniques such as solvent extraction and column chromatography. The compound of formula I can be recovered from the culture filtrate by extraction at a pH of about 5 to 9 with a water immiscible solvent such as petroleum ether, dichloromethane, chloroform, ethyl acetate, diethyl ether or butanol, or by hydrophobic interaction chromatography using polymeric resins such as "Diaion HP-20®" (Mitsubishi Chemical Industries Limited, Japan), "Amberlite XAD®" (Rohm and Haas Industries U.S.A.), activated charcoal, or by ion exchange chromatography at pH 5 to 9. The active material can be recovered from the cell mass by extraction with a water miscible solvent such as methanol, acetone, acetonitrile, n-propanol, or iso-propanol or with a water immiscible solvent such as petroleum ether, dichloromethane, chloroform, ethyl acetate or butanol. One other option is to extract the whole broth with a solvent selected from petroleum ether, dichloromethane, chloroform, ethyl acetate, methanol, acetone, acetonitrile, n-propanol, iso-propanol, or butanol. Typically, the active material is extracted with ethyl acetate from the whole broth. Concentration and lyophilization of the extracts gives the active crude material. The compound of formula I can be recovered from the crude material by fractionation using any of the following techniques: normal phase chromatography (using alumina or silica gel as stationary phase; and eluents such as petroleum ether, ethyl acetate, dichloromethane, acetone, chloroform, methanol, or combinations thereof); reverse phase chromatography (using reverse phase silica gel such as dimethyloctadecylsilyl silica gel, (RP-18) or dimethyloctylsilyl silica gel (RP-8) as stationary phase; and eluents such as water, buffers [for example, phosphate, acetate, citrate (pH 2 to 8)], and organic solvents (for example, methanol, acetonitrile, acetone, tetrahydrofuran, or combinations of these solvents); gel permeation chromatography (using resins such as Sephadex LH-20® (Pharmacia Chemical Industries, Sweden), TSKgel® Toyopearl HW (TosoHaas, Tosoh Corporation, Japan) in solvents such as methanol, chloroform, acetone, ethyl acetate, or their combinations, or Sephadex® G-10 and G-25 in water); or by counter-current chromatography (using a biphasic eluent system made up of two or more solvents such as water, methanol, ethanol, iso-propanol, n-propanol, tetrahydrofuran, acetone, acetonitrile, methylene chloride, chloroform, ethyl acetate, petroleum ether, benzene, and toluene). These techniques may be used repeatedly, alone or in combination. A typical method is chromatography over normal phase using silica gel.

The compound of formula I and isomers thereof, can be converted into their pharmaceutically acceptable salts and derivatives, like esters and ethers, which are all contemplated by the present invention.

The biodegradable lipid used in the formulation is dipalmitoylphosphatidylcholine (DPPC), which is a naturally occurring phospholipid of the endogenous lung surfactant system. Other non-limiting examples of biodegradable lipids that can be used in combination with DPPC include DPPG (Dipalmitoyl phosphatidyl glycerol), DPPE (dipalmitoylphoshatidylethanolamine), cholesterol, phosphatidyl inositol, and phosphotidyl serine.

In another aspect of the invention, the size of the microparticles of the formulation ranges between 0.5 microns and 10 microns.

In yet another aspect of the invention, 90% of the microparticles of the formulation are of size less than 10 microns.

In yet another aspect of the invention, the formulation is an aqueous liposomal dispersion.

In an aspect of the invention, the pH of the formulation is from 6 to 7.

In another aspect, the osmolality of the formulation is from 300 mOsmol/kg to 400 mOsmol/kg. In yet another aspect of the invention, the phase transition temperature of the formulation is from 41° C. to 43° C. In another aspect of the invention, the formulation can be aerosolized to a mass median aerodynamic diameter of 1 μm to 10 μm by using a nebulizer.

The types of nebulizers which can be used include but are not limited to Jet nebulizers, Ultrasonic wave nebulizers and Vibrating Mesh nebulizers.

The present invention also relates to the process for preparation of the microparticle formulation.

In an aspect of the invention, the process for preparation of the formulation involves use of "Solvent evaporation method" which includes the following steps:

(a) dissolving compound of formula I and DPPC (1:15 to 1:25 ratio) in 3 mL to 15 mL chloroform to obtain a solution;

(b) adding 20 mL to 45 mL of methanol to the solution of step (a) and mixing well to obtain homogeneous solution;

(c) adding 20 mL to 50 mL of simulated lung fluid (SLF) to the solution of step (b);

(d) evaporating the solvents;

(e) making up the volume obtained in step (d) to 30 mL with SLF and centrifuging at 15000 G TO 35000 G, at 4° C. for ten minutes to obtain a pellet;

(f) resuspending the pellet obtained in step (e) in SLF to obtain a suspension of concentration 0.5 mg/mL to 10 mg/mL;

(g) filtering the suspension obtained in step (f) through a 0.5 μm-5 μm polycarbonate filter to obtain uniform particle size of the microparticles formed.

The "Solvent evaporation method" used herein is a modification of the method reported in U.S. Pat. No. 4,877,561.

In an embodiment of the invention, in the step (a) of the process for preparation of the microparticle formulation, the compound of formula I and DPPC are dissolved in a 1:20 ratio.

In another embodiment of the invention, in the step (a) of the process for preparation of the microparticle formulation, the compound of formula I and DPPC are dissolved in 5 to 10 mL of chloroform to obtain a solution.

In an embodiment of the invention, in the step (b) of the process for preparation of the microparticle formulation, 30 to 40 mL of methanol is added.

In another embodiment of the invention, in the step (c) of the process for preparation of the microparticle formulation, 25 to 35 mL of SLF is added. In another embodiment of the invention, in the step (e) of the process for preparation of the microparticle formulation, centrifugation is performed at 20,000 to 30,000 G.

In another embodiment of the invention, in the step (f) of the process for preparation of the microparticle formulation, the pellet is resuspended in SLF to obtain a suspension of concentration 1 to 5 mg/mL.

In another embodiment of the invention, in the step (g) of the process for preparation of the microparticle formulation, the suspension obtained in step (f) is filtered through 2 μm to 5 μm polycarbonate filter.

In another aspect of the invention, the process for the preparation of the formulation is a "Solvent free lipid self assembly method" which includes the following steps:
(i) adding 20 mL to 45 mL of SLF to a mixture of compound of formula I and DPPC (1:15 to 1:25 ratio);
(ii) subjecting the mixture of step (i) to 100 rpm to 200 rpm rotation at 42° C. to 45° C. for one hour to obtain a suspension;
(iii) centrifuging the suspension obtained in step (ii) at 15000 G-35000 G at 4° C. for ten minutes to obtain a pellet;
(iv) resuspending the pellet obtained in step (iii) in SLF to obtain a suspension of concentration 0.5 mg/mL to 10 mg/mL; and
(v) filtering the suspension obtained in step (iv) through 0.5 μm-5 μm polycarbonate filter to obtain uniform particle size of the microparticles formed.

In an embodiment of the invention, in the step (i) of the process for preparation of the microparticle formulation, 30 mL to 40 mL of SLF is added to a mixture of compound of formula I and DPPC.

In another embodiment of the invention, in the step (i) of the process for preparation of the microparticle formulation, the compound of formula I and DPPC are dissolved in 1:20 ratio.

In an embodiment of the invention, in the step (iii) of the process for preparation of the microparticle formulation, the suspension obtained in step (ii) is centrifuged at 20,000 G to 35,000 G at 4° C. for ten minutes to obtain a pellet.

In another embodiment of the invention, in the step (iv) of the process for preparation of the microparticle formulation, the pellet obtained in step (iii) is resuspended in SLF to obtain a suspension of concentration 1 mg/mL to 5 mg/mL.

In another embodiment of the invention, in the step (v) of the process for preparation of the microparticle formulation, the suspension obtained in step (iv) is filtered through 2 μm to 5 μm polycarbonate filter.

The present invention further relates to the use of the formulation in a method of treatment of pulmonary tuberculosis, MDRTB, MRSA pneumonias and MSSA pneumonias by administering therapeutically effective amount of the formulation to a mammal in need thereof.

The present invention further relates to the use of the microparticle formulation comprising compound of formula I and a biodegradable lipid for drug delivery wherein the ratio of drug to lipid (compound of formula I) is 1:15 to 1:25 for the manufacture of a medicament for the treatment of pulmonary tuberculosis, MDRTB, MRSA pneumonias and MSSA pneumonias.

In an aspect of the invention, the method of treatment targets alveolar macrophages, which can harbour the mycobacteria and methicillin resistant as well as methicillin sensitive *Staphylococcus aureus*.

The present invention also relates to a method of delivering the microparticle formulation to a mammal in need thereof, wherein the formulation is administered by inhalation or intratracheal instillation for pulmonary delivery.

In an aspect of the invention, the method of delivering the microparticle formulation is by inhalation.

In another aspect of the invention, the method of inhalation is nebulization in which the compound of formula I is entrapped in the microparticles.

In respect of the microparticle formulation of the present invention it has been observed that when administered by inhalation significant concentration of the compound of formula I contained in the formulation is detected in the lungs of mice. However, no significant concentration of compound of formula I is detected in the lungs of mice that received the unformulated compound of formula I. This is indicative of increased bioavailability of the compound of formula I in the microparticle formulation. Further, it has been observed that the drug (compound of formula I) is retained in the lungs over a period of 24 hours when the microparticle formulation of the present invention is administered by inhalation.

In another aspect of the invention, the retention of the entrapped compound of formula I is greater than 30%. Particularly, retention of the entrapped compound of formula I range from 30% to 70%.

The dosage of compound of formula I for inhalation ranges between 0.05 and 10 mg/kg body weight/day.

In another aspect of the invention, the method of delivering the microparticle formulation is intratracheal instillation in a patient on ventilatory support system.

In another aspect of the invention, administration by nebulization helps reduce the amount of compound of formula I required for the treatment of pulmonary tuberculosis, MDRTB, MRSA pneumonias and MSSA pneumonias.

In yet another aspect of the invention, the method helps compound of formula I reach the lungs.

The efficacy of the microparticle formulation has been established by biological assays which are described in detail in subsequent examples. These examples are herein provided for the purpose of illustration only and are not intended to limit the scope of the invention.

EXAMPLES

The following terms/abbreviations/chemical formulae are employed in the Examples
NaCl: Sodium chloride
$CaCl_2$: Calcium chloride
NaOH: Sodium hydroxide
SLF: Simulated lung fluid
HPLC: High Performance Liquid Chromatography
DPPC: 1,2-dipalmitoyl-sn-glycero-3-phosphocholine
DMSO: Dimethyl Sulfoxide
RB flask: Round bottomed flask rpm: Rotations per minute
DSC: Differential Scanning calorimeter
TSI: Twin Stage Impinger
MSSA: Methicillin Sensitive *S. aureus*
MRSA: Methicillin Resistant *S. aureus*
VRE: Vancomycin Resistant Enterococci
TSA: Tryptose Soya Agar
CFU: Colony Forming Units,
HBSS: Hanks Buffered Salt Solution
MTS: (3-(4,5-dimethylthiazol-2-yl)-5-(3-carboxymethoxyphenyl)-2-(4-sulfophenyl)-2H-tetrazolium)
GC-HS: Gas Chromatograph with Head Space Attachment
CPCSEA: Committee for the Purpose of Control and Supervision of Experiments on Animals
IAEC: Institutional Animal Ethics Committee
API: Active Pharmaceutical Ingredient Example 1

Isolation of Culture No. PM0626271 from Soil Collected from Antarctic Region a) Composition of the isolation medium:
Modified artificial sea water agar: Peptone 1.5 g, yeast extract 0.5 g, ferric chloride 0.007 g, 1.0 L water (750 mL artificial sea water+250 mL demineralised water), agar powder 15.0 g, final pH (at 25° C.) 7.4 to 7.8.
Composition of the artificial seawater: Sodium chloride 24.6 g, potassium chloride 0.67 g, calcium chloride.$2H_2O$ 1.36 g, magnesium sulphate.$7H_2O$ 6.29 g, magnesium chloride.$6H_2O$ 4.66 g, sodium bicarbonate 0.18 g, demineralised water 1.0 L, final pH (at 25° C.) 7.8 to 8.2.
b) Procedure:
From Schirmacher Oasis region in Antarctica area, surface level soil was collected and was stored at −20° C. throughout the journey to Piramal Life Sciences Limited, Goregaon, Mumbai, India. The sample was stored at −20° C. to −22° C. and later thawed to room temperature (25±2° C.) for isolation of the microbes. The soil sample (~1 g) was suspended in 25 mL of sterile 1% peptone water in a 100 mL sterilized flask. The flask was vortexed for 30 seconds. Serial dilutions up to $10^{-5}$ were prepared in sterile 1% peptone water. 100 µL of $10^{-5}$ dilution was surface spread on modified artificial seawater agar. The plate was incubated at room temperature (25±2° C.) till colonies were observed. After incubation for one and a half month, the colony which appeared on this medium was streaked on petri plates containing actinomycete isolation agar [Hi Media] prepared in 75% artificial sea water [Accumix™] (AS-AIA). The isolate was purified and was provided culture ID number PM0626271. The culture no. PM0626271 was thus isolated from amongst the growing microorganisms as single isolate.

Example 2

Purification of Culture No. PM0626271 a) Composition of the purification medium (Actinomycete Isolation Agar, agarified by 1.5% agar agar):
Glycerol 5.0 mL, sodium caseinate 2.0 g, L-asparagine 0.1 g, sodium propionate 4.0 g, dipotassium phosphate 0.5 g, magnesium sulphate 0.1 g, ferrous sulphate 0.001 g, 1.0 L water (750 mL Artificial Sea Water+250 mL demineralised water), agar powder 15.0 g, final pH (at 25° C.) 7.4 to 7.8.
Composition of the artificial seawater: Sodium chloride 24.6 g, potassium chloride 0.67 g, calcium chloride.$2H_2O$, 1.36 g, magnesium sulphate.$7H_2O$ 6.29 g, magnesium chloride.$6H_2O$ 4.66 g, sodium bicarbonate 0.18 g, demineralized water 1.0 L, final pH (at 25° C.) 7.8 to 8.2.
b) Procedure:
The culture no. PM0626271 was streaked on Actinomycete Isolation Agar (containing 75% artificial sea water salts) petriplate. The petriplate was incubated for 10 days at 25° C. One of the isolated colonies from the petriplate was transferred to fresh slants of Actinomycete Isolation Agar prepared in 75% artificial seawater. The slants were incubated for 10 days at 25° C.

Example 3

Maintenance of Producer Strain—Culture No. PM0626271 a) Composition of the medium (Actinomycete Isolation Agar):
Glycerol 5.0 mL, sodium caseinate 2.0 g, L-asparagine 0.1 g, sodium propionate 4.0 g, dipotassium phosphate 0.5 g, magnesium sulphate 0.1 g, ferrous sulphate 0.001 g, 1.0 L water (750 mL artificial sea water+250 mL demineralised water), agar powder 15.0 g, final pH (at 25° C.) 7.4 to 7.8.
Composition of the artificial sea water: Sodium chloride 24.6 g, potassium chloride 0.67 g, calcium chloride.$2H_2O$ 1.36 g, magnesium sulphate.$7H_2O$ 6.29 g, magnesium chloride.$6H_2O$ 4.66 g, sodium bicarbonate 0.18 g, demineralized water 1.0 L, final pH (at 25° C.) 7.8 to 8.2.
b) After dissolving the ingredients thoroughly by heating, the resultant solution was distributed in test tubes and sterilized at 121° C. for 30 minutes. The test tubes were cooled and allowed to solidify in a slanting position. The agar slants were streaked with the growth of culture no. PM0626271 by a wire loop and incubated at 27° C. to 29° C. until a good growth was observed. The well-grown cultures were stored in the refrigerator at 4° C. to 8° C.

Example 4

Fermentation of the Culture No. PM0626271 in Shake Flasks a) Composition of seed medium [AS-274 (1)]:
Glucose 15 g, corn steep liquor 5 g, peptone 7.5 g, yeast extract 7.5 g, calcium carbonate 2.0 g, sodium chloride 5.0 g, volume made with 750 mL artificial sea water and 250 mL demineralised water.
b) The above medium was distributed in 40 mL amounts in 500 mL capacity Erlenmeyer flasks and autoclaved at 121° C. for 30 minutes. The flasks were cooled to room temperature (25° C.±2° C.) and each flask was inoculated with a loopful of the well-grown producing strain (culture no. PM0626271) on the slant and shaken on a rotary shaker for 72 hours at 230 rpm to 250 rpm at 30° C.±° C. to give seed culture.
c) Composition of the production medium [AS 36P (1)]:
Soluble Starch 20 g, glucose 15 g, yeast extract 2 g, peptone 3 g, calcium carbonate 2 g, ammonium sulfate 0.5 g, corn steep liquor 2 g, sodium chloride 2 g, magnesium phosphate 5 g, cobalt chloride 1 mL/L from stock of 1 g/L, trace salt solution 1 mL/L, volume made to 1 L using with 75% artificial sea water and 25% demineralized water.
d) 40 mL of the production media in 500 mL capacity Erlenmeyer flasks was autoclaved at 121° C. for 30 minutes, cooled to 29° C. to 30° C. and seeded with 5% (v/v) of the seed culture mentioned in Example 4b.

e) Fermentation parameters:
The production flasks were incubated on shaker at 29° C. and 220 rpm for 96 hours. The production flasks were harvested and the whole broth from each media flask was extracted with equal volume of methanol under shaking condition for one hour at 29° C. and centrifuged at 3500 rpm for half an hour. The supernatant was used for antibacterial agar well diffusion assay for monitoring of the activity.

Example 5

Preparation of Seed Culture in Shake Flasks for Fermentation a) Composition of the medium [AS-274 (1)]:
Glucose 15 g, corn steep liquor 5 g, peptone 7.5 g, yeast extract 7.5 g, calcium carbonate 2.0 g, sodium chloride 5.0 g, volume made with 750 mL Artificial Sea Water and 250 mL demineralised water.
b) The above medium was distributed in 200 mL amounts in 1000 mL Erlenmeyer flasks and autoclaved at 121° C. for 30 minutes. The flasks were cooled to room temperature (25±2° C.) and each flask was inoculated with a loopful of the well-grown producing strain (PM0626271) on the slant and shaken on a rotary shaker for 70 hours to 74 hours at 230 rpm to 250 rpm at 29° C. to 30° C. to obtain the seed culture.

Example 6

Cultivation of the Culture No PM0626271 in Fermenter a) Composition of the production medium:
Artificial Sea Water (artificial sea water salt 28.32 g) (75%), soluble starch 20 g, glucose 15 g, yeast extract 2 g, peptone 3 g, calcium carbonate 2 g, ammonium sulphate 0.05 g, corn steep liquor 2 g, sodium chloride 2 g, magnesium phosphate 5 g, cobalt chloride (cobalt chloride 1 g demineralized water 1.0 L) 1 mL/L, trace salt solution (copper sulphate 7 g, ferrous sulphate 1 g, manganese chloride 8 g, zinc sulphate 2 g, demineralized water 1.0 L) 1 mL/L, demineralized water 1.0 L, pH 6.5 to 7.5 (before sterilization).
b) 100 L of the production medium in 150 L fermenter along with 30 mL of desmophen as an antifoaming agent was sterilized in situ for 30 minutes at 121° C., cooled to 29° C. to 30° C. and seeded with 2.5 L to 3.5 L of the seed culture obtained above (Example 5).
c) Fermentation parameters: The fermentation was carried out at temperature 29° C. to 30° C., agitation 100 rpm, aeration 60 lpm and harvested at 70 hours to 74 hours. The production of the compound of formula I in the fermentation broth was detected qualitatively by testing the bioactivity against *S. aureus* E710 (MRSA strain) and/or *Enterococcus faecium* R2 (VRE) using the agar well diffusion method. The harvest pH of the culture broth was 7.5 to 8.0. After the harvest, whole broth was subjected to solvent extraction.

Example 7

Isolation and Purification of the Compound

The whole broth (10 L batch) was extracted using ethyl acetate (1:1). The organic and aqueous layers were separated. The organic layer was processed to evaporate the solvent to obtain crude ethyl acetate extract (1.5 g). The crude extract was further processed by flash chromatography (silica gel, 30 g, solvent: methanol/chloroform step gradient, flow: 15 mL/minute). The active compound eluted with 1% methanol to 5% methanol in chloroform, which was concentrated to obtain the semipure compound (250 mg). Further purification was carried out by repeated normal phase preparative HPLC.
Preparative HPLC Conditions:
Column: Eurospher silica (10μ, 20×250 mm)
Eluent: methanol:chloroform (5:95)
Flow rate: 20 mL/minute
Detection (UV): 245 nm
Retention time: (5 to 6 minutes)
Purity of fractions was checked by bioassay against *E. faecium* R2 and/or *S. aureus* 3066 and/or analytical HPLC. The eluates were pooled and concentrated under reduced pressure to remove the solvent to obtain the compound.
Analytical HPLC Conditions:
Column: Eurospher RP-18, (3μ, 4.6×125 mm)
Solvent system: Gradient (0% acetonitrile to 100% in 15 minutes against water, followed by 100% acetonitrile for 5 minutes)
Flow rate: 1 mL/minute
Detection (UV): 245 nm
Retention time: compound of formula I (12 to 13 minutes)
Physical & Spectral properties of the compound of formula I:
Appearance: White powder
Melting point: 240° C. (decomposes)
Solubility: Soluble in chloroform, ethyl acetate, methanol and insoluble in water
HR-ESI: 1650.4858 (M+H)
Molecular weight (ESI): 1650.5 (M+H)
Molecular formula $C_{71}H_{83}N_{19}O_{18}S_5$
IR (KBr): 3386, 2927, 1648, 1507, 1206, 756, 666 $cm^{-1}$
$^1$H NMR: refer to Table 1
$^{13}$C NMR: refer to Table 2

TABLE 1

$^1$H NMR of the compound of formula I in $CDCl_3$:$CD_3OD$ (4:1) at 500 MHz

| Peak | δ |
|---|---|
| 1 | 0.7(d, 3H) |
| 2 | 0.74(d, 3H) |
| 3 | 0.95(d, 3H) |
| 4 | 1.04(s, 3H) |
| 5 | 1.08(d, 3H) |
| 6 | 1.2(d, 3H) |
| 7 | 1.28(d, 3H) |
| 8 | 1.34(d, 3H) |
| 9 | 1.37(m, 1H) |
| 10 | 1.5(d, 3H) |
| 11 | 1.6(d, 3H) |
| 12 | 2.1(m, 1H) |
| 13 | 2.2 (m, 1H) |
| 14 | 2.2(m, 1H) |
| | 3.99(m, 1H) |
| 15 | 2.8(d, 1H) |
| 16 | 3.05(t, 1H) |
| | 3.5(t, 1H) |
| 17 | 3.49(d, 2H) |
| 18 | 3.67(d, 1H) |
| 19 | 3.7 (q, 1H) |
| 20 | 4.33(d, 1H) |
| 21 | 4.33(d, 1H) |
| 22 | 4.62((q, 1H) |
| 23 | 4.86(dd, 1H) |
| 24 | 5.19 (s, 1H) |
| 25 | 5.19(s, 1H), |
| | 5.67 (s, 1H) |
| 26 | 5.2(t, 1H) |
| 27 | 5.6(d, 1H) |
| 28 | 5.62(s, 1H), |
| | 6.44(s, 1H) |

TABLE 1-continued $^1$H NMR of the compound of formula I in CDCl$_3$:CD$_3$OD (4:1) at 500 MHz

| Peak | δ |
|---|---|
| 29 | 5.65(d, 2H) |
| 30 | 5.72(s, 1H), 6.61(s, 1H) |
| 31 | 6.1(q, 1H) |
| 32 | 6.25(m, 1H) |
| 33 | 6.28(d, 2H) |
| 34 | 6.8(d, 1H) |
| 35 | 6.91(s, 1H) |
| 36 | 6.94(s, 1H) |
| 37 | 7.2(s, 1H) |
| 38 | 7.43(s, 1H) |
| 39 | 7.45(s, 1H) |
| 40 | 7.65(s, 1H) |
| 41 | 7.87(s, 1H) |
| 42 | 8.05(s, 1H) |
| 43 | 8.17(s, 1H) |
| 44 | 8.2 (s, 1H) |
| 45 | 8.5 (s, 1H) |
| 46 | 8.67 (s, 1H) |
| 47 | 8.99 (s, 2H) |
| 48 | 9.72 (s, 1H) |
| 49 | 9.8 (s, 1H) |

TABLE 2

$^{13}$C NMR of the compound of formula I in CDCl$_3$:CD$_3$OD (4:1) at 500 MHz

| Signal | δ |
|---|---|
| 1 | 12.11 |
| 2 | 13.74 |
| 3 | 14.1 |
| 4 | 14.8 |
| 5 | 16.48 |
| 6 | 17.11 |
| 7 | 17.27 |
| 8 | 17.55 |
| 9 | 20.9 |
| 10 | 23.13 |
| 11 | 27.56 |
| 12 | 27.56 |
| 13 | 29.04 |
| 14 | 33.24 |
| 15 | 46.17 |
| 16 | 50.14 |
| 17 | 51.3 |
| 18 | 53.91 |
| 19 | 53.91 |
| 20 | 55.8 |
| 21 | 57.32 |
| 22 | 58.8 |
| 23 | 62.42 |
| 24 | 62.73 |
| 25 | 64.45 |
| 26 | 64.73 |
| 27 | 65.69 |
| 28 | 65.95 |
| 29 | 70.27 |
| 30 | 77.1 |
| 31 | 101.45 |
| 32 | 101.45 |
| 33 | 102.6 |
| 34 | 116.52 |
| 35 | 120.63 |
| 36 | 121.59 |
| 37 | 123.28 |
| 38 | 123.87 |
| 39 | 123.87 |
| 40 | 125.48 |
| 41 | 126.03 |
| 42 | 126.69 |
| 43 | 128.24 |
| 44 | 130.34 |
| 45 | 130.98 |
| 46 | 131.14 |
| 47 | 132.39 |
| 48 | 141.85 |
| 49 | 144.61 |
| 50 | 148.17 |
| 51 | 148.45 |
| 52 | 151.89 |
| 53 | 152.76 |
| 54 | 155.45 |
| 55 | 157.9 |
| 56 | 159.0 |
| 57 | 160.04 |
| 58 | 160.36 |
| 59 | 161.01 |
| 60 | 163.75 |
| 61 | 164.46 |
| 62 | 164.5 |
| 63 | 166.6 |
| 64 | 167.13 |
| 65 | 167.95 |
| 66 | 168.47 |
| 67 | 168.67 |
| 68 | 170.35 |
| 69 | 170.35 |
| 70 | 171.63 |
| 71 | 172.0 |

Example 8

Estimation of Solubility of Compound of Formula I in SLF (pH 7.4)

Materials Used:
NaCl: RFCL Limited, India
CaCl$_2$: RFCL Limited, India
NaOH: RFCL Limited, India
Procedure:

SLF was prepared by method based on Respiratory Physiology & Neurobiology, 2008, 162, 73-79.

Preparation of SLF 9 g of sodium chloride, 0.220 g of calcium chloride and 6.5 g of lactose were dissolved in 1000 mL of water. The pH of the resultant solution was adjusted to 7.4. Solubility of compound of formula I in SLF was measured at two temperatures, 45° C. and 60° C. For this, 1 mg of compound of formula I was added to 3 mL of SLF (in duplicates) and after vortexing for few seconds was incubated in water bath set at the required temperatures. Solubility was measured at one hour intervals for three hours. The solution was filtered through 0.22 μm filter and the filtrate was injected on HPLC. Solubility was calculated with respect to appropriate calibration curve. Results obtained are given in Table 3.

TABLE 3

| Temperature | Solubility (μg/mL) | | |
|---|---|---|---|
| | 1 hour | 2 hours | 3 hours |
| 45° C. | 1.3 | 0.9 | 1.2 |
| 60° C. | 0.6 | 0.7 | 1.3 |

Conclusion:

Compound of formula I exhibits poor solubility in SLF at 45° C. and 60° C. The solubility is also not time dependent. Compound of formula I is a water insoluble compound, thus solubility was measured in the buffer SLF.

Example 9

Preparation of the Microparticle Formulation of the Compound of Formula I

Materials Used:
DPPC: Avanti Polar Lipids, Canada
Methanol: RFCL Limited, India
Chloroform: RFCL Limited, India
DMSO: RFCL Limited, India
NaCl: RFCL Limited, India
$CaCl_2$: RFCL Limited, India
NaOH: RFCL Limited, India
Lactose monohydrate: Signet Chemical Corporation Private Ltd, USA
Glassware: Merck Limited, India
Glass beads: N.M. Enterprises, India
Polycarbonate membrane filters: ISOPORE™, Millipore, USA
Polypropylene filter holders: SWINNEX®, Millipore, USA
Gas tight glass syringe with metal leur lock: Hamilton Company, USA
pH meter: Eutech instruments, USA
Procedure:
Method A
Solvent Evaporation Method The assay was carried out based on the reference U.S. Pat. No. 4,877,561.

The compound of formula I and DPPC, in ratios of 1:1, 1:10 and 1:20 w/w, were dissolved in 5 mL chloroform in a glass beaker. 30 mL of methanol was added and the mixture was transferred to a 250 mL round bottomed flask. 30 mL of SLF was poured into the mixture slowly. The solvents were evaporated by using a rotary evaporator (Buchi GMBH, Switzerland). The water bath was set at 45° C. and rotation was set at 100 rpm. The vacuum controller was set to a pressure of 400 mBar. Evaporated solvents were collected in a glass solvent collector. The remaining solution in the RB flask turned milky indicating formation of liposomes. Volume of the suspension from the RB flask was made up to 30 mL with SLF, centrifuged at 25,000 G at 4° C. for 10 minutes. The pellet obtained was resuspended in SLF, vortexed and filtered through 1.2 μm polycarbonate filter eleven times to ensure uniform particle size and stored at 4° C. The microparticle formulation was analyzed by optical microscopy and electron microscopy.
Method B
Solvent Free Lipid Self Assembly Method The aim is to develop a solvent free manufacturing process for the formulation. 20 mg of compound of formula I and 20 mg of DPPC (1:20 w/w) were added to a RB flask containing 20 to 30 glass beads and 30 mL of SLF. The mixture was subjected to rotation of 100 rpm at a temperature of 45° C. for one hour. The formulation obtained was subjected to centrifugation and filtration as described in Method A.

The formulation was analyzed by optical microscopy.
Observations:

For microparticles in formulation prepared by Method A.
 (i) Formulation of microparticles containing compound of formula I and DPPC in the ratio of 1:1 w/w and 1:10 w/w exhibited non-homogenous, unstable suspension with drug aggregates when observed under optical microscope. The microparticles settled at the bottom of the tube.
 (ii) Formulation of microparticles containing compound of formula I and DPPC in the ratio of 1:20 w/w exhibited homogenous suspension with no drug aggregates when observed under optical microscope. The microparticles did not settle down in the tube.
 (iii) Formulation of microparticles containing compound of formula I and DPPC in the ratio of 1:20 w/w exhibited microparticles of size 2 μm to 3 μm when observed under electron microscope.

Result:

Formulation of microparticles containing compound of formula I and DPPC is optimally formed using drug:lipid ratio of 1:20 w/w.

Example 10

Determination of entrapment efficiency and mass balance of compound of formula I in the formulation of Example 9 Method A and formulation of Example 9 Method B.
Materials Used:
Methanol: RFCL Limited, India
DMSO: RFCL Limited, India
Glassware: Merck Limited, India
Autopipettes: Eppendorf GMBH, Germany
Procedure:

The entrapment efficiency of compound of formula I in the formulation of Example 9 Method A and Example 9 Method B were analyzed by HPLC (Agilent, USA). The HPLC conditions are as follows:
Column: Lichrosphere® 100, RP-18e, 150×4.6 mm, 5 μm
Mobile phase: (a) 0.01 M ammonium acetate+0.5% triethylamine in 1000 mL water; pH adjusted to 6.5 with glacial acetic acid
 (b) acetonitrile
Composition: (a):(b)::50:50
Run time: 5 minutes
Column temperature: 25° C.
Injection volume: 20 μL
Retention time: ~3.5 minutes
Solvent: 20% DMSO in methanol Compound of formula I was dissolved in 20% DMSO to obtain 200 μg/mL concentration and was used as reference standard. 100 μL of formulation of Example 9 Method A and 100 μL of formulation of Example 9 Method B separately were pipetted into 2 mL centrifuge tubes and 900 μL of 20% DMSO was added to each tube. The tubes were vortexed which led to the rupture of microparticle matrix and release of entire content of compound of formula I entrapped within the matrix. The samples injected independently on the HPLC were as follows: reference standard, formulation of Example 9 Method A (after rupture of the microparticle matrix) and formulation of Example 9 Method B (after rupture of the microparticle matrix). Mean of the peak areas was considered for calculation.

The entrapment efficiency was determined by the formula:

$$\% \text{ entrapment} = \frac{W}{w} \times 100$$

wherein:
W=amount of drug (compound of formula I) associated/entrapped within the microparticle
w=initial amount of compound of formula I For the mass balance calculation, compound of formula I was recovered from the glassware, filters, all the other labware which was used in the formulation preparation process (Example 9 Method A and Example 9 Method B) and its content was estimated. The polycarbonate filters (Example 9 Method A and Example 9 Method B) were washed with 5 mL of 20% DMSO in methanol. This sample was injected in HPLC as 'membrane residue'.

The RB flask used to prepare the formulation was washed with 10 mL of 20% DMSO in methanol. This sample was injected in HPLC as 'flask residue'.

The reference standard was injected six times on the HPLC and peak areas were noted. The relative standard deviation of six injections of the standard was below 2.0%. The samples were injected in duplicate on the HPLC and mean of the peak areas were considered for calculation.

Results obtained are given in Table 4.

TABLE 4

| Formulation | % entrapment | % mass balance |
| --- | --- | --- |
| Example 9 Method A | 90.8 | 100.3 |
| Example 9 Method B | 76.6 | 94.8 |

Conclusion:

Entrapment efficiency of the formulation is comparatively better when prepared with Method A of Example 9 than when prepared with Method B of Example 9.

Example 11

Determination of Particle Size of Microparticles of Formulation of Example 9 Method A Procedure:

The hydrodynamic diameter and size distribution of microparticles of formulation of Example 9 Method A was determined using Photon Correlation Spectroscopy (DELSA Nano, Beckmann Coulter, USA). 1 mL of formulation was diluted to 10 mL with SLF. 1 mL of this solution was used for determining particle size.

Result:

The mean particle size of microparticles of formulation of Example 9 Method A is 2 µm to 3 µm. For each individual population, the dispersion of the particle size around the mean is about 0.45-0.47.

Table 5 provides the three cut-off diameters. $D_{10}$, $D_{50}$ and $D_{90}$ indicate the average diameter of the 10%, 50% and 90% of the particle population respectively.

TABLE 5

| Formulation | $D_{10}$ | $D_{50}$ | $D_{90}$ |
| --- | --- | --- | --- |
| Example 9 Method A | 1.7 | 3.9 | 7.9 |

Conclusion:

The solvent evaporation method (Example 9 Method A) for compound of formula I lipid based microparticles has led to generation of micron size particles in the range of 1 µm to 10 µm (as depicted in Table 5), with more than 99% particles having particle size less than 10 µm (depicted in Table 6).

TABLE 6

| % of particles | Diameter (µm) |
| --- | --- |
| 90 | 5.6 |
| 99.4 | 6.1 |

Example 12

Determination of pH of Formulation of Example 9 Method A

Procedure:

pH meter (Eutech, USA) was standardized electronically against standard pH buffers of pH 4, 7 and 9. pH of the formulation of Example 9 Method A was determined by using the same pH meter.

Result:

pH of the formulation of Example 9 Method A is 6.14.

Conclusion:

The pH of the formulation of Example 9 Method A is physiologically compatible with administration of the drug (compound of formula I) for a short period of up to 30 minutes of one time nebulization or intratracheal installation.

Example 13

Determination of Osmolality of Formulation of Example 9 Method A

Materials:
Reference solution: Wheecon Instruments Private Limited
Osmometer: Wheecon Instruments Private Limited Procedure:

Osmolality of the formulation of Example 9 Method A was determined by using Osmometer. The Osmometer was standardized using reference solution of 290 mOsmol/kg.

Result:

Osmolality of the formulation of Example 9 Method A is 340 mOsmol/kg.

Conclusion:

The physiological osmolality of body fluids is 300 mOsmol/kg. Any significant change in this osmolality has pathological implications. Administration of large volumes of hyper tonic solutions (significantly higher osmolality) or hypotonic solutions (significantly lower osmolality) causes either excessive loss/gain of fluid leading to pathological conditions of pulmonary and tissue edema or dehydration. Introduction of small amounts of fluids, in aerosol form at normal osmolality concentrations precludes the development of aforementioned pathologies. The formulation of Example 9 Method A has osmolality of 340 mOsmol/kg and hence is within the safe limits.

Example 14

Evaluation of Excipient Compatibility of Compound of Formula I in the Formulation of Example 9 Method A Materials:

Hermetic sealing pans with O-rings: Perkin Elmer India Limited

DSC: Perkin Elmer, USA

Procedure:

50 μL of formulation of Example 9 Method A was pipetted in DSC pan. The sample and empty reference pan (reference standard) was hermetically sealed and placed in Hyper DSC and the temperature program was run as follows:
Temperature program: 0° C. to 50° C.
Heating rate: 5° C./minute
Purge gas: Nitrogen
Flow rate: 30 mL/minute
Result:

Liposomes prepared without compound of formula I exhibited an endotherm with an onset at 41.1° C. This endotherm may be attributed to the transition from ripped gel to liquid crystalline phase. The microparticle formulation exhibited an endotherm at approximately 42.5° C. This shift in onset temperatures may be due to physical interaction of compound of formula I with DPPC liposomes. The shift in the main transition marks the transition of the phospholipid bilayer from a highly hindered well-organized hydrocarbon chain packed state to a state in which some acyl chains show presence of kinks.

Conclusion:

The results exhibit drug-excipient compatibility relationship between the compound of formula I and DPPC. There is absence of significant shift in the endotherm onset temperature as well as absence of peak abolition.

Example 15

Estimation of Solvent Content in the Formulation of Example 9 Method A

Materials:
Methanol (HPLC grade): RFCL Limited, India
Chloroform (HPLC grade): RFCL Limited, India
DMSO(HPLC grade): RFCL Limited, India
Glass GC-HS vials: Perkin Elmer India Limited
Glassware: Merck Limited, India
Procedure:

The experiment was done to study residual solvent content in formulation of Example 9 Method A using GC-HS. This experiment evaluates the feasibility of using the solvent evaporation method (Example 9 Method A) to be used for large-scale commercial production of formulation of Example 9 Method A.

Blank Preparation: 5 mL of DMSO was added to a 20 mL GC-HS glass vial. The vial was crimped with a teflon stopper and aluminum cap. Two such vials were prepared for blank injection.

Standard Preparation: 10 mg of chloroform and 100 mg of methanol were accurately weighed in a 100 mL standard volumetric flask. The solvents were dissolved and volume was made up to 100 mL with DMSO. 5 mL of stock solution was pipetted out in a 20 mL GC-HS glass vial. The vial was crimped with a teflon stopper and aluminum cap. Six such vials were prepared for standard injection.

Sample preparation: 5 mL of DMSO was added to a 20 mL GC-HS glass vial. The vial was placed on an electronic balance and the weight was tared. 500 μL of formulation of Example 9 Method A was added to the glass vial and the weight was accurately noted. The vial was crimped with a teflon stopper and aluminum cap. Three such vials were prepared for sample injection.

Table 7 gives chromatographic conditions and method for estimation of solvent content in the formulation of Example 9 Method A.

TABLE 7

| Instrument | Gas Chromatograph: |
| --- | --- |
| | Make: Perkin Elmer |
| | Model No: Clarus 500 |
| | Head space Sampler: |
| | Make: Perkin Elmer |
| | Model No: Turbo Matrix 40 |
| Column | DB-1 (30 meter × 0.53 mm, 5μ) |
| | Make: Agilent |
| Oven Temperature Programming: | Initial temp. 40° C. (hold for 7 minutes) to 200 @ 20° C./min. (5 minutes hold) |
| Injection Temperature | 220° C. |
| Detector | Flame Ionization Detector |
| Detector Temperature | 250° C. |
| Detector Range | 1 |
| Detector Attenuation: | 5 |
| Carrier Gas | Helium |
| Carrier flow | 2.3 psi |
| Split ratio | 1:10 |
| Run Time | 20 minutes |
| Retention Time | Chloroform ~3 minutes |
| | Methanol ~11 minutes |
| | DMSO ~14 minutes |
| Thermo stating Temperature | 90° C. |
| Needle Temperature | 95° C. |
| Transfer line temperature | 100° C. |
| Pressurization time | 1.0 minutes |
| Thermo stating time | 15 minutes |
| GC Cycle Time | 30 minutes |
| Injection Time | 0.07 minutes |
| Withdrawal Time | 0.20 minutes |

Result:

Table 8 gives a break up of effect of evaporation time on solvent content and entrapment of formulation of Example 9 Method A.

TABLE 8

| Time | methanol (ppm) | chloroform (ppm) | % entrapment | % mass balance |
| --- | --- | --- | --- | --- |
| 1 hour evaporation | 9734.1 | 0.0 | 92.1 | 100.1 |
| 2 hours evaporation | 2742.0 | 0.0 | 91.7 | 99.1 |
| 3 hours evaporation | 1464.7 | 0.0 | 85.0 | 92.4 |

Observation:

It has been observed that evaporation time of 2 hours gives a lower solvent content and desired entrapment and mass balance qualities of the formulation of Example 9 Method A. Also the residual solvent content as detected by GC-HS is below the permissible limit for each individual solvent (permitted daily exposure limit for chloroform is 60 ppm and for methanol is 3000 ppm—(ICH Quality Guidelines, Impurities: Guidelines for Residual Solvents, Q3C(R5), February 2011) for the API solvent content and permissible daily exposure limit for the pharmaceutical product.

Conclusion:

The solvent evaporation method (Example 9 Method A) can be considered as a suitable method to develop this formulation.

Example 16

Nebulization of Formulation of Example 9 Method A

Materials:
Twin Stage Impinger Unit: Copley Scientific, U.K.
Nebulizer: DeVILBISS®, Sunrise Medical, USA
Methanol: RFCL Limited, India
DMSO: RFCL Limited, India
HPLC: Agilent, USA
Electronic Balance: Denver Instruments, USA
Procedure:

TSI Unit was used for this study and was assembled as per the instruction manual. TSI is an in vitro glass model of the human pulmonary tract and is used to quantify in vitro the pulmonary drug deposition potential.

The vacuum pump of the TSI was switched on and the flow meter was used to accurately check the flow of the system. The flow valve on the vacuum pump was adjusted to ensure exact flow specification (28.3 L/min). After calibration of the airflow, the whole unit was disassembled. 7 mL of methanol was added to the upper impinger and 20 mL methanol was added to the lower impinger. The TSI unit was assembled again as per the instruction manual.

5 mL of the formulation of Example 9 Method A was added to the medication cup of the nebulizer. Mouthpiece of the nebulizer was attached to the mouth of the TSI. It was ensured that all parts were fit to avoid any vacuum loss.

The vacuum pump of the TSI was started to ensure uniform airflow. After 30 seconds the nebulizer was started and start time was noted. After exactly 5 minutes, the nebulizer was stopped. The pump was allowed to run for another 30 seconds after which it was switched off. The upper impingement chamber mimics the throat and upper airways and the lower impingement chamber mimics the alveoli.

Methanol was used as a rinsing solvent and the contents of the upper and lower impingement chamber were collected in appropriate standard volumetric flasks. 20% DMSO was added to ensure dissolution of compound of formula I. The final volumes of the volumetric flasks were made up by methanol. The above experiment was repeated with six batches of formulation and two batches of unformulated compound of formula I.

The samples were evaluated at several concentrations starting from:
0.5 mg of compound of formula I in 5 ml formulation of Example 9 Method A—Sample 1;
1 mg of compound of formula I in 5 ml formulation of Example 9 Method A—Sample 2;
2.5 mg of compound of formula I in 5 ml formulation of Example 9 Method A—Sample 3;
5 mg of compound of formula I in 5 ml formulation of Example 9 Method A—Sample 4; and
100 µg/mL of unformulated compound of formula I (only compound of formula I)—Sample 5.

This study was done to understand effect of concentration on in vitro drug deposition. The study was further continued to estimate the amount of drug (compound of formula I) lost to the process of nebulization and hence left behind in the nebulizer cup.

Compound of formula I deposited in the upper and lower impingement chamber of the TSI was analyzed by an HPLC with gradient pump and autosampler. The chromatographic conditions used in HPLC analysis are provided in Table 9.

TABLE 9

| Column | Lichrosphere ® 100, RP-18e, 150 × 4.6 mm, 5 µm |
|---|---|
| Mobile Phase Composition | A) 0.01M ammonium acetate + 0.5% triethylamine in 1000 mL water; pH adjusted to 6.5 with glacial acetic acid<br>B) acetonitrile<br>A:B :: 50:50 (Isocratic) |
| Run Time | 5 minutes |
| Column Temperature | 25° C. |
| Injection Volume | 20 µL |
| Retention Time | ~3.5 minutes |
| Solvent | 20% DMSO in methanol |

100 µg/mL of compound of formula I (2.5 mg of compound of formula I was dissolved in 20% DMSO in methanol) was used as reference standard.

The reference standard was injected six times on the HPLC and peak areas were noted. The relative standard deviation of six injections of the standard was below 2.0%. The samples were injected in duplicate on the HPLC and mean of the peak areas were considered for calculation.

Result:

The % of compound of formula I deposited by the various samples (samples 1 to 6) in the upper and lower impinger of the TSI is provided in Table 10.

TABLE 10

| | % compound of formula I deposited | | |
|---|---|---|---|
| Samples | Upper impinger | Lower impinger | Total |
| Sample 1 | 4.5 | 13.4 | 17.9 |
| Sample 2 | 5.8 | 10.4 | 16.2 |
| Sample 3 | 2.6 | 7.8 | 10.5 |
| Sample 4 | 1.4 | 3.7 | 5.1 |
| Sample 5 | 0.0 | 0.0 | 0.0 |

(B) Amount (µg) of compound of formula I lost (during nebulization process) in the nebulization cup is provided in Table 11.

TABLE 11

| Samples | compound of formula I lost in nebulization cup (µg) | % retention of entrapped compound of formula I |
|---|---|---|
| Sample 1 | 222.9 | 56 |
| Sample 2 | 580.9 | 42 |
| Sample 3 | 1706.2 | 32 |
| Sample 4 | 3146.7 | 37 |
| Sample 5 | 5000.0 | 0 |

Observations:

The formulation when nebulized at a concentration of 1 mg/mL and 2.5 mg/mL deposits about 16% and 10% of the initial amount of compound of formula I introduced into the nebulizer cup. The minimum inhibitory concentration of compound of formula I is in the range of 0.125 µg/mL to 5 µg/mL (PCT application publication WO2011027290). The amount of compound of formula I deposited is sufficient and above the minimum inhibitory concentration in the in vitro model. The results suggest that 1 mg/mL and 2.5 mg/mL compound of formula I formulation concentrations could be the concentrations which need to be evaluated in the in vivo studies. At concentrations lower than 1 mg/mL, the percentage of compound of formula I deposited is higher but the quantity is not significant while at concentration of 5 mg/mL, significant amount of compound of formula I is retained back in the nebulizer cup leading to wastage of compound of formula I.

Conclusion:

The results clearly establish that the formulation of Example 9 Method A is capable of depositing significant amount of compound of formula I in the TSI in vitro lung model while the unformulated compound of formula I is not deposited in the TSI on nebulization. Thus the formulation of Example 9 Method A can be used for inhalation-based delivery of compound of formula I.

Biological Evaluation of the Microparticle Formulation

In Vitro Assays

Example 17

Microbial Assay

The assay was carried out based on the reference; Nathan P et al, 1978, Laboratory Methods for Selection of Topical antimicrobial Agents to treat infected Burn Wounds, Burns 4: 177-187.
(A) Bacterial Test Models Used in the Assay:
Staphylococcus aureus 209P (MSSA)
Staphylococcus aureus ATCC 33591 (MRSA)
Enterococcus faecium R-2 (VRE)
(B) Inoculum Preparation Culture from cryovials were streaked on TSA slant and incubated at 37° C. for 18 to 24 hours. Using growth on the slant saline suspension was prepared and the optical density adjusted to 0.3 units at 560 nm (~$10^8$ CFU/ml).
(C) Sample Preparation Samples tested in the assay are:
(i) Sample 1: Unfiltered suspension of the formulation of Example 9 Method B.
(ii) Sample 2: Filtered suspension of the formulation of Example 9 Method B (after filtration through 0.22 μm filter).
(iii) Sample 3: Sample prepared by methanol disruption method: Sample 2 was mixed with equal volumes of methanol and incubated for one hour. Dilutions of this solution were prepared in methanol and used for evaluating the efficacy of the released compound of formula I.
(iv) Sample 4: Unformulated compound of formula I (compound of formula I dissolved in methanol chloroform in 1:80 ratio).
The concentrations of samples 1, 2, 3 and 4 evaluated in the assay were: 100, 50, 25, 12.5, 6.25, 3.125, 1.56, 0.78, 0.39 and 0.195 μg/mL.
(D) Assay Procedure:

40 μL of inoculum suspension of the test culture obtained from (B) was put into each of 40 mL melted TSA butt (maintained at 38° C. to 39° C.) in 100 mL capacity sterile conical flasks and swirled for uniform mixing. The seeded butts were poured into petri plates (150 mm outer diameter) allowing them to set for about 30 minutes. The plates were kept at 4° C. to 8° C. for complete setting. Required numbers of wells (of diameter 6 mm) were punched out from the set medium. 50 μL_of sample 1, sample 2 and sample 3 were added in corresponding wells in the plates. The plates were pre-incubated at low temperature (2° C.-8° C.) for about 30 minutes to allow diffusion. The plates were then incubated at 37° C. for 18 to 24 hours. Vancomycin at 20 μg/mL was used as standard antibiotic. The results of activity of various samples were interpreted as size of zone of inhibitions in mm.

Result:

Sample 3 showed clear zones from 100 μg/mL to 0.78 μg/mL while sample 4 showed clear zones from 100 μ/mL to 0.39 μg/mL.

The activity (with respect to zone size) of sample 2 is better than sample 1 as sample 2 showed clear zone of inhibition at 12.5 μg/ml while sample 1 showed clear zones at 25 μg/ml.

In case of sample 3, the zone size of compound of formula I is less than the unformulated compound of formula I (sample 4). This may be due to the slow release of compound of formula I from the lipid formulation.

Conclusion:

The activity of compound of formula I released from the formulation of Example 9 Method B (sample 3) is comparable to the unformulated compound of formula I (sample 4) and hence can be carried forward for in vivo testing and evaluation.

Example 18

In Vitro Cytocompatibility Assay

The assay was carried out based on the reference Journal of Biomedical Materials Research, 2009, 89A, 281-292.

This assay was performed to evaluate the cytocompatibility of the formulation of Example 9 Method A with the relevant cell lines and standard cells which are specified by the regulatory agencies.
Cell Lines Evaluated:
MRC5 (Lung fibroblast cell line)
A549 (Type II alveolar cell line isolated from of malignant tumour)
L929 (Mouse fibroblast cell line, is an ASTM standard)
Experimental Details:
Cell density: 10,000/well for MRC 5 and L292, and 3000/well for A549
Time points: 24 hours and 48 hours.
Concentrations Evaluated:
1, 0.7, 0.3, 0.1 mg/mL for microparticles of formulation of Example 9 Method B—Sample 1
0.3, 0.1 mg/mL for microparticles without compound of formula I, DPPC—Sample 2
0.1, 0.01 mg/mL for only compound of formula I—Sample 3
Procedure:

The toxicological evaluation was done using The CellTiter 96 Aqueous One Solution Assay by Promega (Cat. no: G3582). The assay is a standard colorimetric method for determining the number of viable cells in proliferation or cytotoxicity assays. The MTS used in the assay is bioreduced by cells into a colored formazan product that is soluble in tissue culture medium. The quantity of formazan product as measured by the amount of 490 nm absorbance is directly proportional to the number of living cells in culture.

Briefly, the cell lines were plated in triplet with 96-well plate and allowed to adhere and proliferate over a period of 24 hours. 24 hours after cell adhesion, the compounds were added. 48 hours post cell plating, the assay was terminated by replacing the medium with 100 μL fresh medium, and addition of 20 μL of CellTiter 96 Aqueous One Solution (Promega, Cat. no: G3582). A set up in triplet of "no-cell" control containing 100 μL of culture medium and 20 μL of "One Solution" was also maintained as control in the assay. The plate was incubated for 30 minutes to 4 hours for the color to develop. The ELISA 96-well plate was then subjected to absorbance recordings at 490 nm (450-540 nm) with a 96-well plate reader. The average 490 nm absorbance from the "no-cell" control was subtracted from all other absorbance values and the corrected absorbance was utilized for further calculations. (Background absorbance from "no-cell" control is typically 0.2 to 0.3 absorbance units after 4 hours of incubation).

Result:

Viability of all the cell lines evaluated in presence of the Sample 1 was more than 98%. The morphology of the cell lines was unaltered and monolayer confluence was present. This shows that at the evaluated concentrations the sample 1 did not exhibit any toxicity in the cell-based assay. Compound of formula I in its unformulated form however exhibited cytotoxicity in all the different cell lines evaluated. Hence the formulation has an additional advantage of limiting the toxicity manifested by compound of formula I. The results are summarized in Table 12.

TABLE 12

| | % cell viability | | | | | |
|---|---|---|---|---|---|---|
| | MRC5 | | L929 | | A549 | |
| Samples | 24 hours | 48 hours | 24 hours | 48 hours | 24 hours | 48 hours |
| Sample 1 | 96 | 100 | 96 | 100 | 100 | 93 |
| Sample 2 | 100 | 100 | 100 | 100 | 100 | 100 |
| Sample 3 | 70 | 0 | 73 | 0 | 95 | 0 |

Conclusion:

Sample 3 has the potential to result or express in vivo adverse effects and toxicity. However sample 1 that includes the use of DPPC, the toxic potential of compound of formula I is masked and biological efficacy is observed in absence of toxicity.

Example 19

In Vitro Macrophage Uptake Assay

The assay was carried out based on the reference Respiratory Research, 2009, 10, 44.

Isolation and Culture of Rat Alveolar Macrophages:

Bronchoalveolar lavage washings from the rats were taken after appropriate ethical permission. Sterile warmed saline was introduced into the lung and then removed by suction. Bronchoalveolar lavage fluid was transported on icepacks (usually 100 to 200 mL of bronchoalveolar lavage fluid per donor is desired). The fluid was subjected to centrifugation at 250 g for 10 minutes and the cells were collected. Pooled the cell pellets by resuspending the cells in a total of 10 mL of HBSS. 100 µL aliquot was removed and stained with Wright-Giemsa stain to do a differential cell count. The cell count was adjusted and plated the cells in macrophage culture medium (HAM F12 medium, Amimed, Switzerland). 0.5 mL of the cell suspension was added to each of the 6 well tissue culture plates with 0.5 mL of the macrophage culture medium. The cells were incubated for 24 hours at 37° C. and 5% $CO_2$. Cell adherence and cell growth was evaluated and treated with the formulation of Example 9 Method A tagged with sulforhodamine dye. Post treatment the cells were evaluated for fluorescence. This fluorescence results for selective uptake of the formulation by the alveolar macrophages.

Result:

The microparticles of formulation of Example 9 Method A were selectively taken up by the alveolar macrophages starting from 1-hour post treatment. The dye shows gradual saturation in intensity at 3 hours. This is indicative of active uptake and a saturation point of the uptake. The mycobacteria reside and survive in the alveolar macrophages, hence it is very critical to ensure that the drug reaches the macrophages. By the designed microparticle formulation of Example 9 Method A it is evident that not only is compound of formula I reaching the macrophages but is being actively taken up by them, which is desired for the therapy to be successful in vivo.

The Formulation of Example 9 Method A is actively taken up (gradual increase in the compound concentration) and metabolized by the macrophages (decrease in the compound concentration) as evident from the values in table 12. The free drug (compound of formula I) does not show active uptake (evident from the saturated concentrations of the free drug).

TABLE 12

| | 30 minutes (µg/mL) | 60 minutes (µg/mL) | 120 minutes (µg/mL) |
|---|---|---|---|
| Formulation of Example 9 Method A | 1.26 | 4.26 | 2.62 |
| Compound of formula I | 2.01 | 2.01 | 1.99 |

Conclusion:

Compound of formula I when developed as a lipid based microparticle formulation is actively taken up by the alveolar macrophages, which are the target for treatment. The therapy has the potential to actively reach the target and relevant cells.

In Vivo Assay

Animals used in the experiments were housed and cared for, in accordance with the Guidelines in force published by CPCSEA, Tamil Nadu, India. Procedures using laboratory animals were approved by the IAEC of Piramal Life Sciences Limited, Goregaon, Mumbai, India.

Example 20

Lung Deposition Studies

The assay was done as reported in The AAPS Journal, 2005, 7 (1), E20-E41.

A pilot in vivo lung deposition study was carried out as per the reference mentioned. Guinea pigs were divided in three groups. Group 1 received formulation of Example 9 Method A, group 2 received unformulated compound of formula I and group 3 was untreated (naïve group). 10 mg/kg of the formulation was aerosolized and the animals were allowed to breathe passively. Following administration of the formulation of Example 9 Method A the animals were sacrificed at 30 minutes time point. The lungs were collected and analyzed by HPLC. HPLC conditions are shown in Table 13.

TABLE 13

| HPLC System | Waters Alliance HPLC |
|---|---|
| Column | BDS Hypersil, C18 (250 × 4.6 mm) 5µ |
| Mobile phase | A—Acetonitrile, B—0.5% Formic Acid pH 3.5 with TEA |
| Flow | 1 mL/min |
| Gradient program (Time/% A) | 0.01/20, 10/80, 13/80, 15/20, 17/20 |

TABLE 13-continued

| | |
|---|---|
| Injection Volume | 50 L |
| Column Temperature | 25° C. |
| Wavelength | 240 nm |
| Retention Times | compound of formula I - 10.21 min |

Results obtained are summarized in Table 14.

TABLE 14

| Groups | compound of formula I deposited (ng/g) |
|---|---|
| Group 1 | 320 ± 0.05 |
| Group 2 | 0 |
| Group 3 | 0 |

Observations:

On nebulization, the unformulated compound of formula I is unable to reach the lungs. The formulation of Example 9 Method A was able to reach the lungs on passive respiration. Further exposure of the animals will lead to increased levels of compound of formula I in the lungs.

Conclusion:

The formulation of Example 9 Method A is able to reach the lungs.

Example 21

Determination of Pulmonary Bioavailability of the Formulation of Example 9 Method A The assay was done as reported in The AAPS Journal, 2005, 7 (1), E20-E41.

A nose-only exposure in vivo lung deposition study was carried out as per the reference mentioned. Guinea pigs were divided in two groups. Group 1 received unformulated compound of formula I (3 mg/kg) and group 2 received formulation of Example 9 Method A (3 mg/kg). The unformulated compound of formula I and formulation of Example 9 Method A were aerosolized and the nose-only exposure was carried out using jet nebulizer wherein the nebulization period was one hour. Following aerosol administration, the animals were sacrificed at 1 hour, 2 hours, 6 hours, 12 hours and 24 hours post aerosol exposure and the lungs were collected and analyzed to quantitate the amount of compound of formula I (ng/g) deposited in the lung by LC-MS. LC-MS conditions are specified below:

TABLE 15

| Chromatographic Conditions: | |
|---|---|
| LC-MS System: | Shimadzu UFLC XR - AB Sciex API4000 |
| Column: | Thermo BDS, C18, 100 × 4.6 mm, 5 μm |
| Mobile phase: | A: 5 mM Ammonium Formate (pH 3.5) + 0.1% Acetic Acid |
| | B: Acetonitrile |
| | A:B :: 20:80% v/v |
| Flow rate: | 1.0 mL/min |
| Injection volume: | 5.0 μL |
| Polarity: | Positive |
| Run time: | 3.00 min |
| Retention time: | Compound of formula I: 2.11 min |
| Extraction solvent | Ethyl acetate |
| Reconstitution solution | 200 μL Methanol |

TABLE 16

| Source/Gas parameters: | |
|---|---|
| Parameter | Value |
| Collision Gas (CAD) | 7.00 |
| Curtain Gas (CUR) | 25.00 |
| Ion source Gas 1 (GS1) | 50.00 |
| Ion source Gas 2 (GS2) | 55.00 |
| Ion Spray Voltage (ISV) | 5500.00 |
| Capillary Temperature | 500.00 |

TABLE 17

| MS-MS Parameters: | | | | | |
|---|---|---|---|---|---|
| Parent mass | Product mass | Declustering potential (DP) | Entrance potential (EP) | Collision cell exit potential (CXP) | Collision energy (CE) |
| 1650.400 (Compound of formula I) | 1247.400 | 120.00 | 10.00 | 28.00 | 75.00 |

Results obtained are summarized in Table 18.

| | Compound of formula I deposited (ng/g) | |
|---|---|---|
| Time interval | Group 1 | Group 2 |
| 1 hour | 1 | 361.89 |
| 2 hours | 1 | 213.74 |
| 6 hours | 1 | 217.13 |
| 12 hours | 1 | 176.86 |
| 24 hours | 1 | 147.55 |

Observations

On nebulization, the unformulated compound of formula I was unable to reach the lungs. The formulation of Example 9 Method A was able to reach the lungs and was retained for 24 hours.

Conclusion

The formulation of Example 9 Method A was able to overcome the poor bioavailability profile of unformulated compound of formula I. Further the lung retention profile of formulation of Example 9 Method A can also make it suitable for once a day inhalation.

Example 22

Evaluation of cumulative accumulation of formulation of Example 9 Method A after once a day dosing for 5 days for nebulization exposure period of 1 hour/day The assay was done as reported in The AAPS Journal, 2005, 7 (1), E20-E41.

A nose-only exposure in vivo lung deposition study was carried out as per the reference mentioned. Guinea pigs were divided in two groups. Group 1 received unformulated compound of formula I (3 mg/kg) and group 2 received formulation of Example 9 Method A (3 mg/kg). The unformulated compound of formula I and formulation of Example 9 Method A were aerosolized and the nose-only exposure was carried out using jet nebulizer wherein the nebulization period was one hour everyday for five consecutive days and the animals were sacrificed on 6th day. The lungs were collected and analyzed to quantitate the amount of compound of formula I (ng/g) deposited in the lung by LC-MS. LC-MS conditions are as provided in Tables 15, 16 and 17 of Example 21.

Results obtained are summarized in Table 19.

| Groups | Compound of formula I deposited (ng/g) |
|---|---|
| Group 1 | 1 |
| Group 2 | 885.59 |

Observations:

On nebulization, the unformulated compound of formula I was unable to reach the lungs. The formulation of Example 9 Method A was able to reach the lungs and retain for 24 hours and also exhibit compound of formula I after chronic daily exposure for 5 days.

Conclusion:

The capability of the lungs to retain the compound of formula I as formulation (formulation of Example 9 Method A) for five days can be used as five days of nebulization as a therapeutic regimen.

Example 23

To evaluate dose scheduling of the formulation of Example 9 Method A The assay was done as reported in The AAPS Journal, 2005, 7 (1), E20-E41.

A nose-only exposure in vivo lung deposition study was carried out as per the reference mentioned. Guinea pigs were divided in three groups. Group 1 received unformulated compound of formula I (3 mg/kg); group 2 received formulation of Example 9 Method A (3 mg/kg) once a day for one day and group 3 received formulation of Example 9 Method A (3 mg/kg) twice a day for one day. The unformulated compound of formula I and formulation of Example 9 Method A were aerosolized and the nose-only exposure was carried out using jet nebulizer. The animals were sacrificed and the lungs were collected and analyzed to quantitate the amount of compound of formula I (ng/g) deposited in the lung by LC-MS. LC-MS conditions are as provided in Tables 15, 16 and 17 of Example 21.

Results obtained are summarized in Table 20.

| Groups | Compound of formula I deposited (ng/g) |
|---|---|
| Group 1 | 0 |
| Group 2 | 361.89 |
| Group 3 | 1210.8 |

Observations:

On nebulization, the unformulated compound of formula I was unable to reach the lungs. The formulation of Example 9 Method A was able to reach the lungs and the amount of compound of formula I absorbed by the lungs increased as the dose was doubled in a day.

We claim:

1. A microparticle formulation comprising a compound of formula I;

Formula I and a biodegradable lipid for drug delivery wherein the ratio of the compound of formula I to lipid is 1:15 to 1:25; wherein said formulation is a biodegradable and inhalable formulation.

2. The microparticle formulation as claimed in claim 1, wherein compound of formula I constitutes 1% to 5% (w/w) of the formulation.

3. The microparticle formulation as claimed in claim 1, wherein the biodegradable lipid is dipalmitoylphosphatidylcholine (DPPC).

4. The microparticle formulation as claimed in claim 1, wherein the particle size of the microparticles ranges between 0.5 and 10 microns.

5. The microparticle formulation as claimed in claim 4, wherein at least 90% of the microparticles are of particle size less than 10 microns.

6. The microparticle formulation as claimed in claim 1, wherein the formulation is an aqueous liposomal dispersion.

7. The microparticle formulation as claimed in claim 1, wherein the formulation has a pH ranging from 6 to 7.

8. The microparticle formulation as claimed in claim 1, wherein for the formulation the phase transition temperature of ranges from 41° C. to 43° C.

9. A process for the preparation of a microparticle formulation comprising the compound of formula I as defined in claim 1 and dipalmitoylphosphatidylcholine (DPPC) wherein the ratio of compound of formula I to DPPC is 1:15 to 1:25, wherein said process comprises the steps of:
 (a) dissolving compound of formula I and DPPC in 3 mL to 15 mL chloroform to obtain a solution;
 (b) adding 20 mL to 45 mL of methanol to the solution of step (a) and mixing well to ensure homogeneity;
 (c) adding 20 mL to 50 mL of simulated lung fluid (SLF) to the solution of step (b);
 (d) evaporating the solvents;
 (e) making up the volume obtained in step (d) to 30 mL with SLF and centrifuging at 15000 G TO 35000 G at 4° C. for ten minutes to obtain a pellet;
 (f) resuspending the pellet obtained in step (e) in SLF to obtain a suspension of concentration 0.5 mg/mL to 10 mg/mL; and (g) filtering the suspension obtained in step (f) through 0.5 μm-5 μm polycarbonate filter to obtain uniform particle size of the microparticles formed.

10. The process as claimed in claim 9, wherein the particle size of the microparticles ranges between 0.5 and 10 microns.

11. The process as claimed in claim 10, wherein at least 90% of the microparticles are of size less than 10 microns.

12. A process for the preparation of the microparticle formulation comprising the compound of formula I as defined in claim 1 and dipalmitoylphosphatidylcholine (DPPC) wherein the ratio of compound of formula I to DPPC is 1:15 to 1:25, wherein said process comprises the steps of:
   (i) adding 20 mL to 45 mL of simulated lung fluid (SLF) to a mixture of compound of formula I and dipalmitoylphosphatidylcholine (DPPC);
   (ii) subjecting the mixture of step (i) to 100 rpm to 200 rpm rotation at 42° C. to 45° C. for one hour to obtain a suspension;
   (iii) centrifuging the suspension obtained in step (ii) at 15000 G-35000 G at 4° C. for ten minutes to obtain a pellet;
   (iv) resuspending the pellet obtained in step (iii) in SLF to obtain a suspension of concentration 0.5 mg/mL to 10 mg/mL; and
   (v) filtering the suspension obtained in step (iv) through 0.5-5 μm polycarbonate filter to obtain uniform particle size of the microparticles formed.

13. A method for the treatment of pulmonary tuberculosis, multi drug resistant tuberculosis, methicillin resistant *Staphylococcus aureus* pneumonias or methicillin sensitive *Staphylococcus aureus* pneumonias, comprising administering by inhalation to a mammal in need thereof a therapeutically effective amount of the microparticle formulation as claimed in claim 1.

14. The method as claimed in claim 13, wherein said method targets alveolar macrophages.

15. A method of delivering microparticle formulation as claimed in claim 1 to a mammal in need thereof, wherein the formulation is administered to the mammal by inhalation or intratracheal instillation for pulmonary delivery.

16. The method as claimed in claim 15, wherein the formulation is administered by inhalation.

17. The method as claimed in claim 16, wherein the administration of formulation by inhalation is done by nebulization in which the compound of formula I contained in the formulation is entrapped in microparticles.

18. The method as claimed in claim 16, wherein the dosage for inhalation ranges between 0.05 and 10 mg/kg body weight/day.

19. The method as claimed in claim 16, wherein the compound of formula I, contained in the formulation administered by inhalation is retained in the lungs over a period of 24 hours.

20. The method as claimed in claim 19, wherein the retention of the entrapped compound of formula I range from 30% to 70%.

* * * * *

UNITED STATES PATENT AND TRADEMARK OFFICE
CERTIFICATE OF CORRECTION

| | | Page 1 of 1 |
|---|---|---|
| PATENT NO. | : 8,697,653 B2 | |
| APPLICATION NO. | : 13/813470 | |
| DATED | : April 15, 2014 | |
| INVENTOR(S) | : Geetanjali Chandrashekhar Chimote et al. | |

It is certified that error appears in the above-identified patent and that said Letters Patent is hereby corrected as shown below:

Title Page, Item (73), Assignee: "Priamal" should read --Piramal--.

Signed and Sealed this
Twenty-fourth Day of June, 2014

Michelle K. Lee
*Deputy Director of the United States Patent and Trademark Office*